(12) United States Patent
Brigido et al.

(10) Patent No.: US 12,336,744 B2
(45) Date of Patent: Jun. 24, 2025

(54) DEVICE FOR FIXATING ORTHOPEDIC INJURY

(71) Applicant: Howmedica Osteonics Corp., Mahwah, NJ (US)

(72) Inventors: Stephen A Brigido, Bethlehem, PA (US); Christopher F. Hyer, Columbus, OH (US); Gregory C. Berlet, Westerville, OH (US); Murray J. Penner, Bethlehem, PA (US); Jeffrey D. Sander, Parkville, MO (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 19/041,586

(22) Filed: Jan. 30, 2025

(65) Prior Publication Data

US 2025/0169863 A1  May 29, 2025

Related U.S. Application Data

(63) Continuation of application No. 16/671,832, filed on Nov. 1, 2019, now Pat. No. 12,295,628.
(Continued)

(51) Int. Cl.
*A61B 17/80* (2006.01)
*A61B 17/17* (2006.01)
(Continued)

(52) U.S. Cl.
CPC ...... *A61B 17/8061* (2013.01); *A61B 17/1728* (2013.01); *A61B 17/84* (2013.01); *A61B 2017/681* (2013.01); *A61F 2/4202* (2013.01)

(58) Field of Classification Search
CPC . A61B 17/8061; A61B 17/1728; A61B 17/84; A61B 2017/681; A61F 2/4202
See application file for complete search history.

(56) References Cited

U.S. PATENT DOCUMENTS 8,277,459 B2  10/2012  Sand et al.
8,795,286 B2   8/2014  Sand et al.
(Continued)

FOREIGN PATENT DOCUMENTS

DE  102008004922 A1   7/2009
FR      2764183 A1  12/1998

OTHER PUBLICATIONS

Extended European Search Report with Written Opinion for Application No. 19206836.9 dated Jul. 22, 2020, 14 pages.
(Continued)

*Primary Examiner* — Bruce E Snow
(74) *Attorney, Agent, or Firm* — Lerner David LLP (57) ABSTRACT

A device for use in orthopedic procedures involving the alignment and fixation of bone. The device includes a body having a bone facing surface, an opposing surface, a lateral surface being disposed between the bone facing surface and the opposing surface and a longitudinal axis extending through the bone facing surface and the opposing surface. The body defines a pin hole extending through the body from the bone facing surface to the opposing surface, a bone fastener hole extending through the body from the bone facing surface to the opposing surface, a tool hole extending at least partially through the body and an alignment index for positioning the body relative to bone.

17 Claims, 9 Drawing Sheets

Related U.S. Application Data (60) Provisional application No. 62/754,342, filed on Nov. 1, 2018.

(51) Int. Cl.
  *A61B 17/84* (2006.01)
  *A61B 17/68* (2006.01)
  *A61F 2/42* (2006.01)

(56) References Cited

U.S. PATENT DOCUMENTS

| | | |
|---|---|---|
| 8,882,816 B2 | 11/2014 | Kartalian et al. |
| 8,900,274 B2 | 12/2014 | Tyber et al. |
| 8,992,532 B2 | 3/2015 | Wong et al. |
| 9,011,503 B2 | 4/2015 | Duggal et al. |
| 9,387,019 B2 | 7/2016 | Duggal et al. |
| 9,452,057 B2 | 9/2016 | Dacosta et al. |
| 9,498,265 B2 | 11/2016 | Sammarco |
| 9,603,640 B2 | 3/2017 | Palmer et al. |
| 9,622,805 B2 | 4/2017 | Santrock et al. |
| 9,629,730 B2 | 4/2017 | Reiley |
| 9,636,102 B2 | 5/2017 | Sikora et al. |
| 9,636,157 B2 | 5/2017 | Medoff |
| 9,662,221 B2 | 5/2017 | Surma et al. |
| 9,730,714 B2 | 8/2017 | Lian |
| 9,730,741 B2 | 8/2017 | Makhlouf |
| 9,757,237 B2 | 9/2017 | Mayer et al. |
| 9,814,474 B2 | 11/2017 | Montoya et al. |
| 9,820,787 B2 | 11/2017 | Hilse et al. |
| 9,888,931 B2 | 2/2018 | Bake |
| 9,888,949 B2 | 2/2018 | Johnson et al. |
| 9,936,994 B2 | 4/2018 | Smith et al. |
| 9,949,744 B2 | 4/2018 | McCormick |
| 9,974,588 B2 | 5/2018 | Stemniski et al. |
| 9,993,254 B2 | 6/2018 | Loring et al. |
| 10,004,518 B2 | 6/2018 | Fallin et al. |
| 10,039,559 B2 | 8/2018 | Awtrey et al. |
| 10,045,807 B2 | 8/2018 | Santrock et al. |
| 10,045,862 B2 | 8/2018 | Wong et al. |
| 10,117,685 B2 | 11/2018 | Ehmke et al. |
| 10,130,377 B2 | 11/2018 | Hollis et al. |
| 10,149,687 B2 | 12/2018 | McGinley et al. |
| 10,159,480 B2 | 12/2018 | Tuten |
| 10,182,845 B2 | 1/2019 | Grant |
| 10,238,382 B2 | 3/2019 | Terrill et al. |
| 10,292,735 B2 | 5/2019 | Robinson et al. |
| 11,690,659 B2 * | 7/2023 | Bays ............... A61B 17/152 606/90 |
| 2008/0015587 A1 | 1/2008 | Munoz |
| 2008/0154384 A1 | 6/2008 | Acker et al. |
| 2009/0210011 A1 | 8/2009 | Den Hartog et al. |
| 2010/0211071 A1 | 8/2010 | Lettmann et al. |
| 2014/0236305 A1 | 8/2014 | Olgiati et al. |
| 2014/0324053 A1 | 10/2014 | Stemniski et al. |
| 2016/0100831 A1 | 4/2016 | Hanson et al. |
| 2016/0199076 A1 | 7/2016 | Fallin et al. |
| 2016/0228152 A1 | 8/2016 | Robinson et al. |
| 2016/0235414 A1 | 8/2016 | Hatch et al. |
| 2016/0242791 A1 * | 8/2016 | Fallin ............... A61B 17/151 |
| 2016/0324555 A1 | 11/2016 | Brumfield et al. |
| 2017/0020569 A1 | 1/2017 | Grant |
| 2017/0042599 A1 | 2/2017 | Bays et al. |
| 2017/0056031 A1 | 3/2017 | Awtrey et al. |
| 2017/0071644 A1 | 3/2017 | Steffensmeier et al. |
| 2017/0100140 A1 | 4/2017 | Stemniski et al. |
| 2017/0105775 A1 | 4/2017 | Ricker et al. |
| 2017/0112638 A1 | 4/2017 | Coulange et al. |
| 2017/0128111 A1 | 5/2017 | Johnson et al. |
| 2017/0156743 A1 | 6/2017 | Stemniski et al. |
| 2017/0164989 A1 | 6/2017 | Weiner et al. |
| 2017/0181740 A1 | 6/2017 | Sikora et al. |
| 2017/0181770 A1 | 6/2017 | Reiley et al. |
| 2017/0196575 A1 | 7/2017 | Hanson et al. |
| 2017/0196602 A1 | 7/2017 | Lundquist et al. |
| 2017/0196604 A1 | 7/2017 | Hartdegen et al. |
| 2017/0209193 A1 | 7/2017 | Hartdegen et al. |
| 2017/0215896 A1 | 8/2017 | Stemniski et al. |
| 2017/0216043 A1 | 8/2017 | Surma et al. |
| 2017/0296158 A1 | 10/2017 | Loring et al. |
| 2017/0311984 A1 | 11/2017 | Stecco et al. |
| 2017/0325826 A1 | 11/2017 | Bake et al. |
| 2017/0348030 A1 | 12/2017 | Haddad et al. |
| 2018/0000592 A1 | 1/2018 | Mayer et al. |
| 2018/0070995 A1 | 3/2018 | Kay et al. |
| 2018/0092674 A1 | 4/2018 | McDaniel et al. |
| 2018/0110530 A1 | 4/2018 | Wagner et al. |
| 2018/0146970 A1 | 5/2018 | Luna et al. |
| 2018/0153558 A1 | 6/2018 | Bake et al. |
| 2018/0161080 A1 | 6/2018 | Johnson et al. |
| 2018/0177511 A1 | 6/2018 | Luna et al. |
| 2018/0177513 A1 | 6/2018 | Stemniski et al. |
| 2018/0185079 A1 | 7/2018 | Smith et al. |
| 2018/0193039 A1 | 7/2018 | Dacosta et al. |
| 2018/0193151 A1 | 7/2018 | Fallin et al. |
| 2018/0206861 A1 | 7/2018 | Stemniski et al. |
| 2018/0235643 A1 | 8/2018 | Lins et al. |
| 2018/0250024 A1 | 9/2018 | Woodard et al. |
| 2018/0289380 A1 | 10/2018 | Mauldin et al. |
| 2018/0317942 A1 | 11/2018 | Awtrey et al. |
| 2018/0317992 A1 | 11/2018 | Santrock et al. |
| 2018/0344328 A1 | 12/2018 | McGinley et al. |
| 2019/0015140 A1 | 1/2019 | Dacosta et al. |
| 2019/0059913 A1 | 2/2019 | Saltzman et al. |
| 2019/0059917 A1 | 2/2019 | Saltzman et al. |
| 2019/0059918 A1 | 2/2019 | Saltzman et al. |
| 2019/0083114 A1 | 3/2019 | Hollis et al. |
| 2019/0110818 A1 | 4/2019 | Grant |
| 2019/0133612 A1 | 5/2019 | McGinley et al. |
| 2019/0142487 A1 | 5/2019 | Orsak |
| 2019/0142598 A1 | 5/2019 | Koenig |

OTHER PUBLICATIONS

Partial European Search Report with Examination for Application No. 19206836.9 dated Mar. 16, 2020, 13 pages.

* cited by examiner

DEVICE FOR FIXATING ORTHOPEDIC INJURY

CROSS-REFERENCE TO RELATED APPLICATIONS

This application is a continuation of U.S. application Ser. No. 16/671,832, filed on Nov. 1, 2019, which claims the benefit of the filing date of U.S. Provisional Patent Application No. 62/754,342, filed Nov. 1, 2018, the disclosures of which are hereby incorporated herein by reference.

BACKGROUND OF THE INVENTION

The present invention relates generally to an alignment and fixation device for use during orthopedic surgeries, and more specifically surgeries of the foot and/or ankle, for example, Lisfranc procedures or a Lapidus bunionectomy.

Together, the foot and ankle are composed of 26 bones and 33 joints, along with more than 100 muscles, tendons, and ligaments, all residing beneath a relatively slim covering of soft tissue and skin. Structurally, the foot has three main anatomical regions: the forefoot, the midfoot and the hindfoot. These regions work together with the ankle to provide the body with support, balance and mobility. A structural flaw or malfunction in any one region can manifest in injuries in other regions of the foot or areas of the body.

Foot and ankle injuries typically occur as a result of dropping a heavy object on the top of the foot, stepping on an uneven surface or falling with the foot in a twisted position. Foot and ankle injuries also commonly occur in athletes when the foot is bound and subjected to simultaneous impact and rotation.

A common midfoot injury is a Lisfranc injury. The Lisfranc joint complex is composed of the tarsometatarsal (TMT) joints and the proximal intermetatarsal and anterior intertarsal joint articulation. As a result of its position in the midfoot, the Lisfranc joint provides critical structural support and stability to the transverse arch of the midfoot. Typically, a Lisfranc injury displaces one or more of the metatarsal bones. Treatment of Lisfranc injuries are complicated by the fact that these injuries are often difficult to diagnose due to the range of clinical presentations. Even when properly diagnosed, achieving proper anatomical reduction is challenging due to the intricacies of the bony architecture within the Lisfranc joint.

Treatment typically requires open reduction and internal fixation. Open reduction refers to the surgical repair of a fracture or dislocation to properly realign the bones. Open reduction allows direct visualization and reduction of the fracture-dislocation and enables debridement of the commuted fracture fragments, soft tissue, and osteochondral debris that frequently exist as a result of the traumatic nature of the injury. Internal fixation refers to fixation of screws, plates or intramedullary bone nails and allows for the bone to heal.

Bunions are another common foot deformity. A bunion is a distortion of bones and joints of a person's foot and is associated with hallux abducto valgus, or the movement of the great toe laterally. This condition is often painful and debilitating. Bunions are typically caused by poor biomechanics of the foot and tight footwear, which may aggravate the condition.

A Lapidus bunionectomy is a surgical procedure to remove painful bunions, by reforming the metatarsal. Typically, a bunionectomy surgery involves correction of the foot by reconstructing bones and joints. While there are numerous ways to correct bunions, the most common is an osteotomy, and specifically a chevron osteotomy. In a chevron osteotomy, the bone is cut at the distal end. The cut is made in a V-shape near the distal metacarpal joint, which allows the entire toe to be moved laterally to the correct alignment. A small screw is then fixed to the joint to provide stability while the bone heals.

Studies have shown that achieving and maintaining anatomical reduction is critical for optimal outcomes when performing Lisfranc or Lapidus procedures. Due to the significant operative challenges in treating these foot deformations, it is desirable to use instruments which improve surgical efficiency and the accuracy with which the displaced bones are aligned and fixed.

Therefore, there is a need for an easy to use device that guarantees accurate alignment of fractured bones and allows for internal fixation of the same to facilitate proper healing.

SUMMARY OF THE INVENTION

In accordance with a first aspect of the present invention, a device for use in orthopedic procedures involving the alignment and fixation of bone is provided. The device includes a body having a bone facing surface, an opposing surface, a lateral surface disposed between the bone facing surface and the opposing surface, and a longitudinal axis extending through the bone facing surface and the opposing surface. The body has a first pin hole extending through the body from the bone facing surface to the opposing surface and being sized and configured to receive a pin, a first bone fastener hole extending through the body from the bone facing surface to the opposing surface and being sized and configured to receive a bone fastener, a tool hole extending at least partially through the body and being sized and configured to receive an adjustment tool, and an alignment index for positioning the body relative to bone. The alignment index may assist a surgeon and/or surgical robot in properly positioning the device on the foot of the patient while the structure of the device, and more particularly the bone fastener hole and the tool hole, ensure proper alignment and fixation of displaced bone. The alignment index may be any mechanism of referencing proper alignment, including the use of markers for navigation of the device (for placement by a surgeon or robotically), a side hole extending through the lateral surface in a transverse direction to the longitudinal axis (or in any other appropriate direction), a radiopaque marker at an appropriate location (including in the same position as such side hole), two points provided at appropriate locations to establish a line or axis in an appropriate location to use together as a reference for aligning the device relative to bone (such points being any suitable indicia, radiopaque or holes), or any combination of the foregoing. Moreover, the device allows the surgical procedure to be performed with a relatively small incision to reduce recovery time.

In accordance with another aspect of the invention, a kit for orthopedic surgery is provided. The kit includes an alignment and fixation device and forceps. The alignment and fixation device includes a body with a bone facing surface, an opposing surface, a lateral surface disposed between the bone facing surface and the opposing surface, and a longitudinal axis extending through the bone facing surface and the opposing surface. The device has a pin hole hole extending through the body from the bone facing surface to the opposing surface and being sized and configured to receive a pin, a bone fastener hole extending through the body from the bone facing surface to the opposing surface and being sized and configured to receive a bone fastener, and a tool hole extending through the body from the bone facing surface to the opposing surface and being sized and configured to receive an adjustment tool.

In yet another aspect of the invention, a method of aligning and fixating bone during orthopedic surgery is provided. The method includes obtaining an alignment and fixation device, the device having a body with a bone facing surface, an opposing surface, a lateral surface disposed between the bone facing surface and the opposing surface, and a longitudinal axis extending through the bone facing surface and the opposing surface. The body defines a first hole, a second hole, a third hole and a side hole, each of the first, second and third holes extending through the body from the bone facing surface to the opposing surface while the side hole extends through the lateral surface and into the second hole. The method further comprises the steps of positioning the bone facing surface of the alignment and fixation device on a foot of a patient, inserting a pin through the first hole and into skin of the patient to secure the alignment and fixation device to bone, adjusting bone, using an adjustment device, from a misaligned position to an aligned position and inserting a first bone fastener through the third hole to secure the bone in the aligned position.

DETAILED DESCRIPTION

In describing preferred embodiments of the disclosure, directional anatomical nomenclature will be referenced to describe spatial relationships between different portions of the device. This nomenclature is used for convenience only and is not intended to be limiting with respect to the scope of the invention. For example, when used in connection with the alignment and fixation device, the term "anterior" means towards the front part of the body or the face and the term "posterior" means towards the back of the body when the device is attached to the foot and/or ankle of the patient. The term "medial" means toward the midline of the body and the term "lateral" means away from the midline of the body. The term "term "superior" means towards the head of the patient and the term "inferior" means toward the sole of the foot. When referring to the fixation elements (e.g., screws) or tools used to secure the fixation elements or realign displaced bone, the term "proximal" means closer to the user, wherein as the term "distal" means further from the user.

Figure 1A:
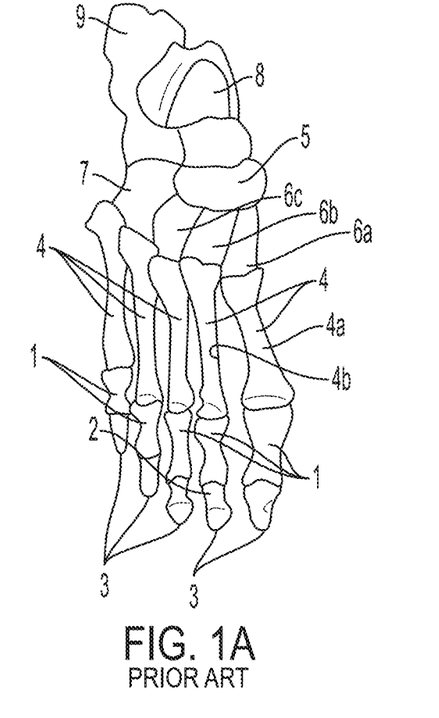
FIG. 1A is top plan view of healthy foot bones.

FIG. 1 illustrates the bone structure of a healthy right foot and is composed of three main regions: the forefoot, the midfoot, and the hindfoot. The forefoot is composed of the five toes, called phalanges and their connecting long bones, called metatarsals. Each toe, except the big toe, is composed of three phalanges (proximal phalange 1, middle phalange 2 and distal phalange 3) and two joints. Each of phalanges 1, 2, 3 are connected to metatarsals 4 by the metatarsal phalangeal joints at the ball of the foot. The big toe has two phalanges (distal phalange 3 and proximal phalange 1) and a joint called the interphalangeal joint. The big toe articulates with the head of the first metatarsal 4a and is called the first metatarsophalangeal joint (MTPJ). Underneath the first metatarsal 4a head are two tiny, round bones called sesamoids.

The midfoot has five irregularly shaped tarsal bones: navicular 5, medial cuneiform 6a, intermediate cuneiform 6b, lateral cuneiform 6c, and cuboid 7. The bones of the midfoot are connected to the forefoot and the hindfoot by muscles and the plantar fascia called arch ligament (not shown).

The hindfoot is composed of the talus 8 (lower ankle) and calcaneus 9 (heel). The superior end of talus 8 is connected to the tibia and fibula (not shown) of the lower leg and forms a hinge that allows the foot to move. Calcaneus 9 joins the talus 8 to form the subtalar joint.

Figure 1B:
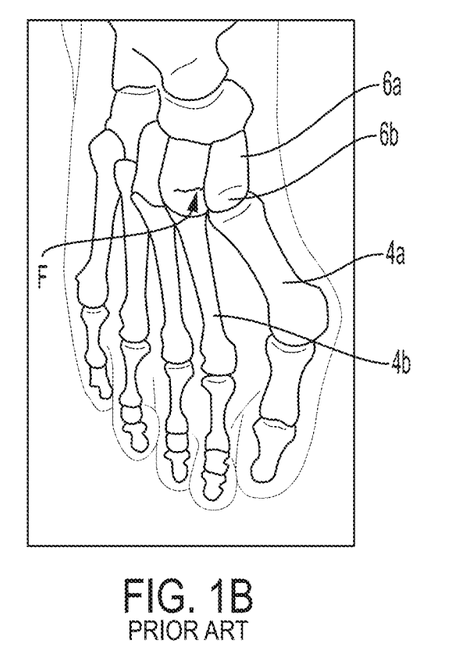
FIG. 1B is top plan view of foot bones having a Lisfranc injury.
Figure 2A:
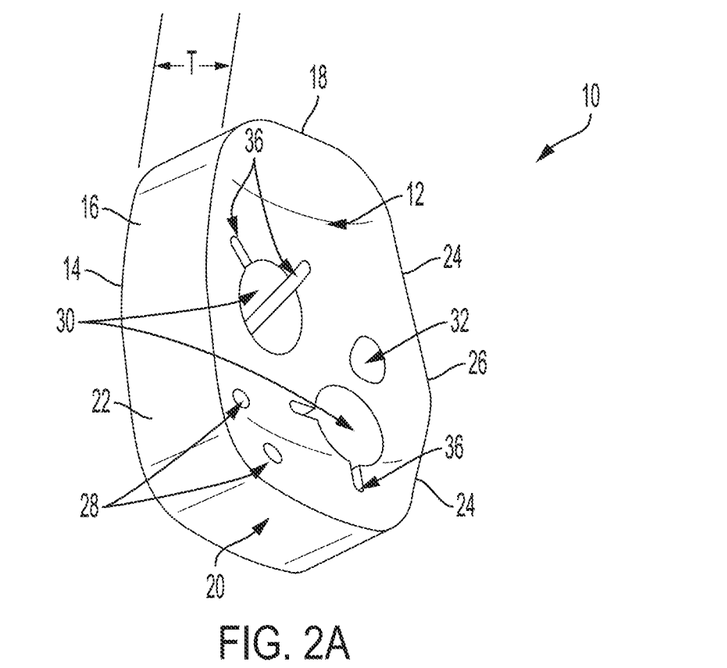
FIGS. 2A-2C are perspective views of an alignment and fixation device in accordance with an embodiment of the present invention.
Figure 2B:
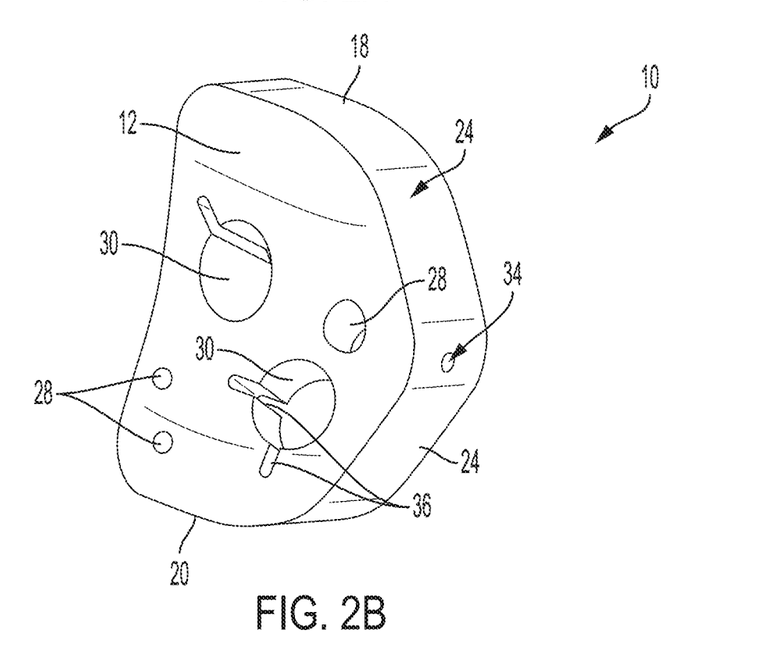
Figure 2C:
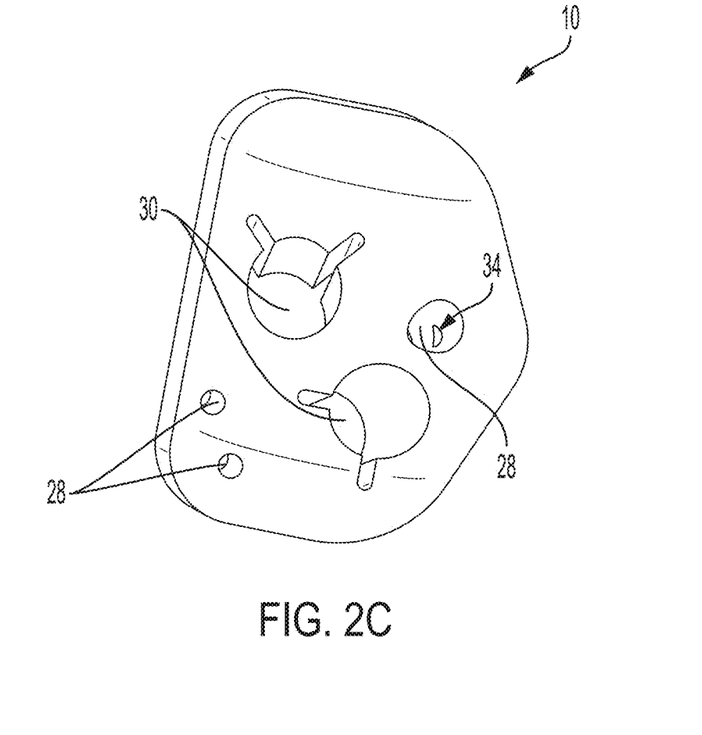
Figure 3:
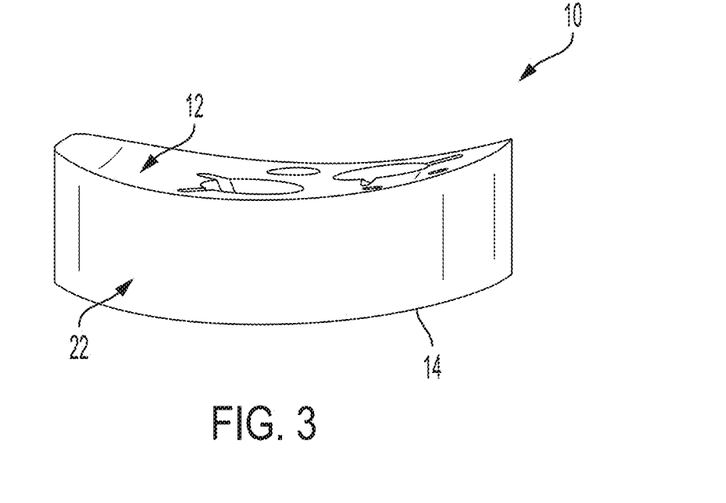
FIG. 3 is a perspective view in a posterior-anterior direction of the alignment and fixation device of FIGS. 2A-2C.
Figure 4A:
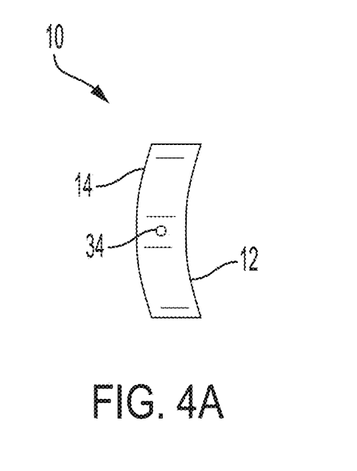
FIG. 4A is a side plan view in an anterior-posterior direction of the alignment and fixation device of FIGS. 2A-2C.
Figure 4B:
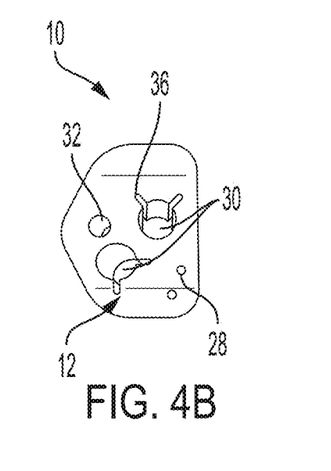
FIG. 4B is a side plan view in a medial-lateral direction of the alignment and fixation device of FIGS. 2A-2C.
Figure 4C:
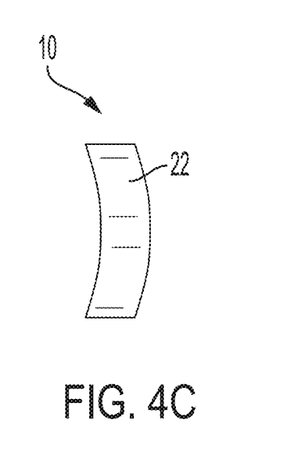
FIG. 4C is a side plan view in a posterior-anterior direction of the alignment and fixation device of FIGS. 2A-2C
Figure 5:
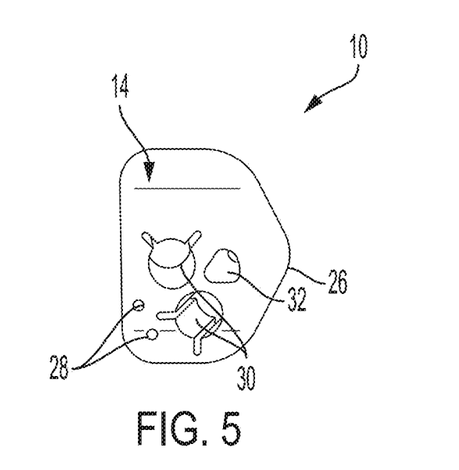
FIG. 5 is a side plan view in a medial-lateral direction of the alignment and fixation device of FIGS. 2A-2C.

Tarsometatarsal articulations are arthrodial joints in the foot, also known as the "Lisfranc joint." The Lisfranc joint is the medial articulation located at the intersection of the first 4a and second metatarsals 4b and the medial 6a and intermediate 6b cuneiforms. The Lisfranc ligament is a large band of plantar collagenous tissue that spans the articulation of the medial cuneiform 6a and the base of the second metatarsal 4b. A Lisfranc injury is an injury to the Lisfranc joint and/or ligament and generally occurs as a result of direct or indirect trauma. The injury may be a dislocation such as a ligament injury, or a fracture and a dislocation. As shown in FIG. 1B, the fracture F usually occurs in the bones of the midfoot and the dislocation generally causes a separation of the joints between the forefoot and the midfoot and results in the misalignment of one or both of the first 4a and second metatarsals 4b relative to the tarsal bones.

FIGS. 2A-5 illustrate an alignment and fixation device 10 for realigning and fixating displaced bone, for example, the metatarsal bones during a Lisfranc procedure. To facilitate understanding, fixation device 10 will be described hereinafter in the context of treating an injury to the Lisfranc joint. It will be appreciated, however, that device 10 may also be used to align and fixate fractures or dislocations of any foot/ankle bone or hand/wrist bone. For example, the alignment and fixation device may be used during surgeries to treat various injuries, including but not limited to a Lapidus bunionectomy, talar fractures, navicular fractures, cuneiform fractures, cuboid fractures, metatarsal base fractures, proximal and distal tibial fractures, distal radius fractures, fractures of the carpal bones, midfoot arthroplasty, hindfoot arthroplasty, and osteotomies of the hindfoot, midfoot and ankle.

Device 10 has a bone contacting surface 12, an opposing surface 14, a lateral surface 16 disposed between the bone contacting surface and the opposing surface and a longitudinal axis passing through the bone contacting surface and the opposing surface. The lateral surface 16 defines a thickness T of the device. In an exemplary embodiment, device 10 has a relatively small thickness T of between approximately 5-100 mm. In other embodiments, device 10 may have a thickness of greater than 100 mm. Device 10 can be made of any suitable material, but is preferably formed of a polymeric or thermoplastic material, for example, a glass-fiber reinforced grade of polyacrylamide (PARA) such as Ixef® GS-1022 Polyarylamide (PARA). In the preferred embodiment, device 10 is intended to be a single use and disposable device. In this manner, device 10 need not be repeatedly sterilized, a process which can alter the shape of the device and thus reduce the accuracy with which the device can carry out a realignment procedure. Nevertheless, in other embodiments, device 10 may be formed from other materials suitable for orthopedic surgeries and capable of being sterilized on multiple occasions.

Device 10 is shaped generally as a pentagonal prism such that lateral surface 16 defines a superior surface 18, an inferior surface 20, a posterior surface 22, angled surfaces 24 and an anterior corner 26. As will be explained in further detail below, the pentagonal shape of the device assists a user in positioning device 10 in the proper location on the patient's midfoot. Device 10 may nevertheless be formed as any other shape, for example, a triangle or a rectangle. Each of the corners may be rounded to avoid pricks to the patient and/or the user.

In one exemplary embodiment, device 10 may have a length (e.g., the distance between superior surface 18 and inferior surface 20) of between approximately 15-200 mm, and a width (e.g., the distance between posterior surface 22 and anterior corner 26) of between approximately 15 mm and 100 mm. For example, the device may be approximately 32 mm in length and approximately 25 mm in width. The dimensions of device 10 may of course be modified based upon the size of the patient and the particular anatomical region upon which the device is intended to be positioned.

The bone contacting surface 12 may be concave in shape relative to a plane passing between the bone facing surface and the opposing surface in a direction orthogonal to the longitudinal axis. Bone contacting surface 12 is thus adapted to be positioned on a medial side of a patient's midfoot, and specifically, on the medial cuneiform 6a. The bone contacting surface 12, however, may be alternatively shaped and/or curved in accordance with the anatomical region upon which the device is intended to be positioned.

The opposing surface 14 may be convex in shape relative to the plane passing through the bone facing surface and the opposing surface in a direction orthogonal to the longitudinal axis. The convex shape of opposing surface 16 is ergonomically shaped and allows the device to be easily gripped during surgery.

The body of device 10 defines at least one pin fixation borehole 28, at least one bone fastening borehole 30, an adjustment tool borehole 32 and an alignment index for positioning the body of the device relative to bone. Pin fixation borehole 28, bone fastening borehole 30 and adjustment tool borehole 32 extend completely through the body of the device from bone contacting surface 12 to opposing surface 14. In a preferred embodiment, device 10 includes at least two pin fixation boreholes 28 for receiving a pin and securing the device to the foot of a patient and two bone fastening boreholes 30 for guiding a bone fastener into bone.

The diameter of each pin fixation borehole 28 may be between approximately 1.6-2.0 mm such that each pin fixation borehole is sized to receive a pin, such as a k-wire, having a diameter of approximately 1.6 mm or approximately 2.0 mm. Pin fixation boreholes 28 may be positioned at any location on the device but are preferably spaced a distance from bone fastening boreholes 30 and adjustment tool borehole 32 so as to not interfere with the bone fasteners or the adjustment tool. By way of example, pin fixation boreholes 28 may be disposed relatively close to one another, for example, adjacent the inferior and posterior sides of device 10, as shown in FIGS. 2A-5. Alternatively, pin fixation boreholes 28 may be positioned substantially on opposite sides of the device as shown in FIGS. 8-12.

A first bone fastening borehole 30 may be positioned at approximately the midline of the device while a second bone fastening borehole 30 may be inferiorly positioned relative to the first bone fastening borehole. For this reason, the first bone fastening borehole is sometimes referred to herein as the superior bone fastening borehole and the second bone fastening borehole is sometimes referred to herein as the inferior bone fastening borehole. Superior bone fastening borehole 30 may be angled in a superior-inferior direction and in a posterior-anterior direction relative to the longitudinal axis. In this manner, when device 10 is secured to the medial cuneiform 6a, the superior bone fastening borehole is adapted to guide a bone fastener, such as a bone screw, through the medial cuneiform 6a, the intermediate cuneiform 6b and the lateral cuneiform 6c. Superior bone fastening borehole 30 may, for example, be angled in the superior-inferior direction at approximately 20 degrees relative to the longitudinal axis of the device, and angled in the posterior-anterior direction at approximately 2.5 degrees. The relatively small posterior-anterior angle ensures that the screw path is biased away from the posterior aspect of the medial cuneiform to prevent breakthrough.

The second or inferior bone fastening borehole 30 may be angled in an inferior-superior direction and a posterior-anterior direction relative to the longitudinal direction of the device. For example, inferior bone fastening borehole 30 may be angled at approximately 20 degrees in the inferior-superior direction and approximately 20 degrees in the posterior-anterior direction. As a result, when device 10 is secured to the medial cuneiform 6a, the inferior bone fastening borehole 30 is adapted to guide a bone screw through the medial cuneiform 6a and into the second metatarsal 4b. Each of the bone fastening boreholes 30 may have a diameter of approximately 7 mm. In a preferred embodiment, the bone fastening boreholes 30 may also include one or more cutting slots 36 sized to receive a cutting tool such as a scalpel.

Adjustment borehole 32 is preferably positioned at the midline of the device and relatively closer to anterior corner 26 than posterior surface 22. Adjustment borehole 32 is sized and shaped to receive a distal tip of an adjustment device such as forceps. In an exemplary embodiment, adjustment borehole 32 is approximately 3.3 mm in diameter.

Alignment index 34 is any mechanism for referencing proper alignment of device 10 with respect to a foot bone of a patient. Alignment index 34 may include, without limitation, indicia on a surface of the device, such as a reference line or an arrow, one or more markers for navigation, a side hole extending through lateral surface 16, two points provided at appropriate locations to establish a line or axis, or any combination of the foregoing to position and align the device on the foot of the patient. It will be appreciated that the indicia, the markers and/or the points may include a radiopaque marker at the appropriate location(s), and for example, may mirror the position of the below described side hole.

In robotic situations, navigation may also be used and alignment may be made via a pre-operative planning step useable with any of the alignment indexes but particularly with a robotic placement.

In situations in which alignment index 34 is a side hole, the side hole may extend through device 10 in a transverse direction (e.g., not parallel) to the longitudinal axis of the device. For example, side hole 34 may extend in an anterior-posterior direction from anterior corner 26 to adjustment borehole 32. Side hole 34 may be between approximately 1.6-2.0 mm in diameter and configured to receive a guidewire such as a k-wire. It will be appreciated that the locations of the at least one pin fixation borehole 28, the at least one bone fastening borehole 30, the adjustment tool borehole 32 and the side hole 34, as well as the sizes and angles of the same, may be modified for treating fractures and/or dislocations elsewhere on the foot or body.

Figure 6:
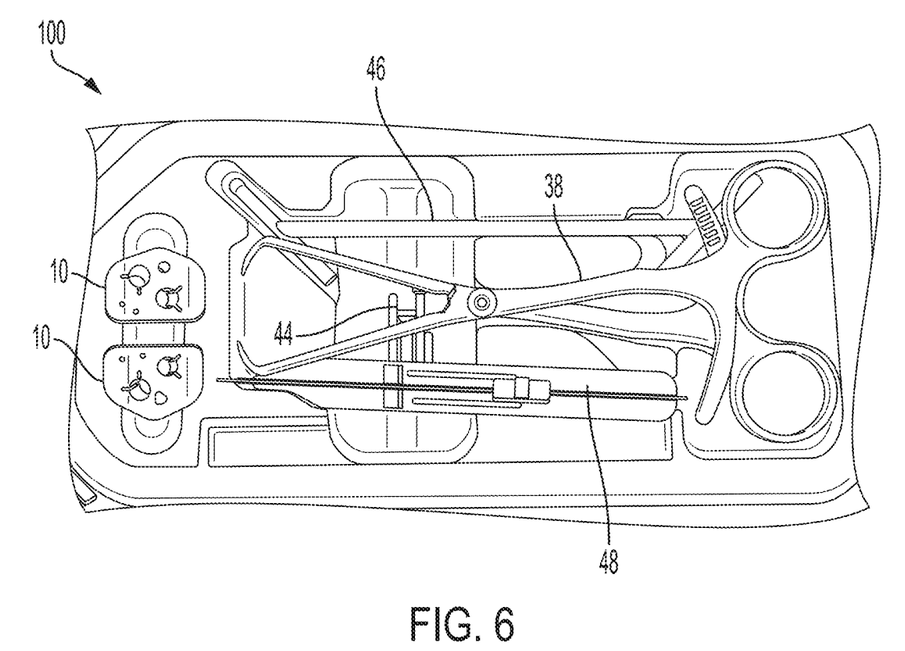
FIG. 6 is top plan view of a kit for treating a Lisfranc injury including the alignment and fixation device of FIGS. 2A-2C.

FIG. 6 illustrates a kit 100 for performing a Lisfranc surgery. The kit may be provided as a sterilized and disposable kit that includes all of the necessary components for performing a Lisfranc surgery. For example, kit 100 may include one or more alignment and fixation devices 10. Preferably, two devices 10 are included in each kit 100, a left device for treating a Lisfranc injury to the left foot and a mirror image right device for treating a Lisfranc injury to a right foot. Kit 100 may also include an adjustment tool such as forceps 38, a plurality of guidewires 40 (shown in FIG. 7), a pin 42 (shown in FIG. 9) for pinning the device to the foot of a patient, one or more bone fasteners such as bone screws 44, a wire guide 46, a depth gauge 48 and a scalpel (not shown).

Figure 7:
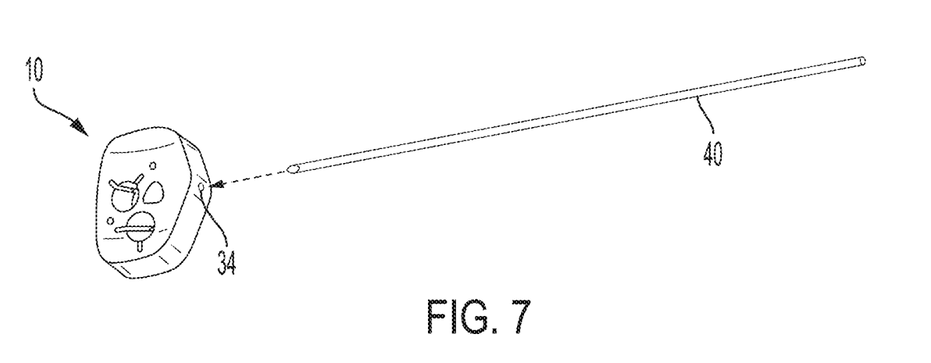
FIGS. 7-12 illustrate the repair of a Lisfranc injury using the alignment and fixation device of FIGS. 2A-2C.

Use of the kit 100 in treating a Lisfranc injury will now be described with reference to FIGS. 7-13. In prepping for a Lisfranc surgery, a surgeon or other user may retrieve a desired one of the right or left devices and a first guidewire 40 from kit 100. As shown in FIG. 7, first guidewire 40 is inserted through side hole 34 until the distal end of the guidewire is positioned within adjustment borehole 32.

Figure 8:
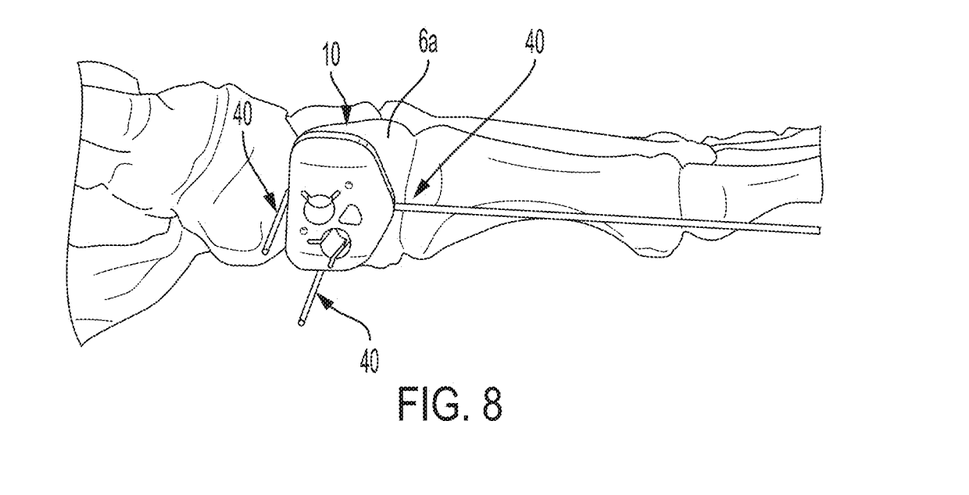

The surgeon may then place a second guidewire 40 percutaneously into the cunconavicular joint of the patient's foot to establish a posterior limit for the alignment and fixation device and a third guidewire percutaneously adjacent an inferior end of the medial cuneiform to establish an inferior limit of the alignment and fixation device. As shown in FIG. 8, the surgeon than places the concave bone contacting surface 12 of device 10 against the patient's skin, adjacent the medial cuneiform 6*a*, with the posterior surface 22 of the device against the second guidewire and the inferior surface 20 of the device against the third guidewire. The surgeon may then adjust the device until the first guidewire is aligned parallel to the longitudinal axis of the first metatarsal 4*a*. It will be appreciated that in other embodiments including other alignment indexes 34 (not shown), device 10 may be properly positioned by aligning the alignment index in parallel to the longitudinal axis of the first metatarsal 4*a* or at another desired position relative to another bone. For example, if the indicia is a reference line provided on a surface of the device and extending in the direction of the side hole, the surgeon may align the reference line along the longitudinal axis of the first metatarsal. Alternatively, if the indicia is an array of markers, the surgeon may manually align the markers or use known navigation techniques in concert with the assistance of a surgical robot to align the markers and the midline of the device along the first metatarsal of the patient.

Figure 9:
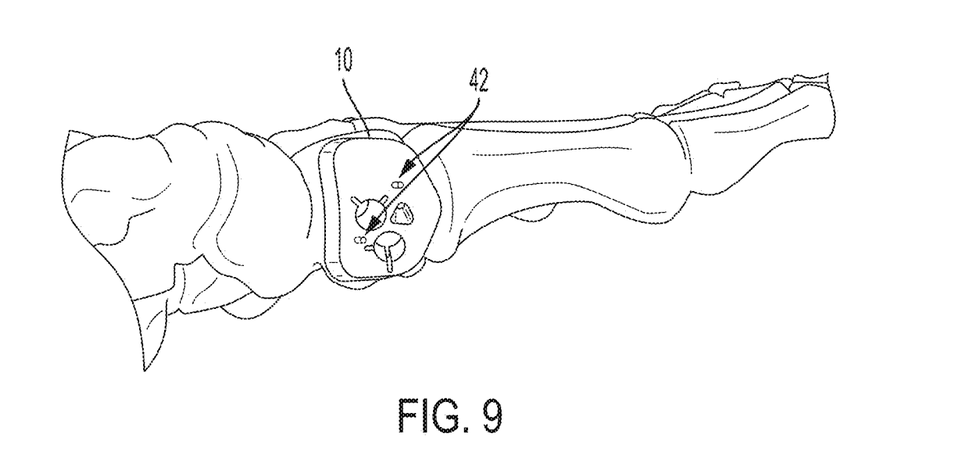

One or more pins 42 are then inserted through pin fixation borcholes 28, through the patient's skin and into bone to temporarily secure the device to the midfoot of the patient. The pins may be bent or trimmed, as shown in FIG. 9, in order to improve access to bone fastening borcholes 30 and adjustment borehole 32.

Figure 10:
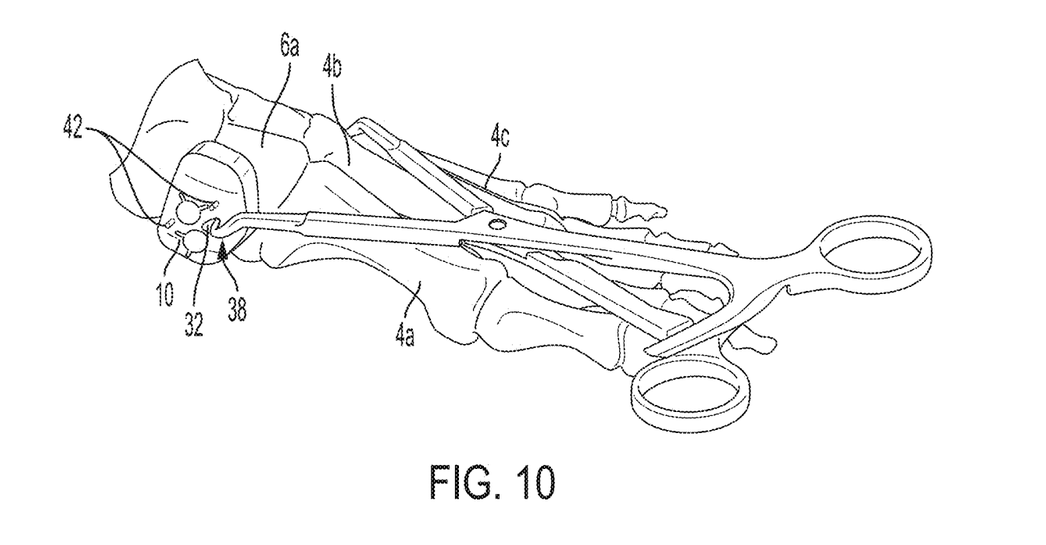

After the device has been secured to the foot of the patient, the surgeon may then retrieve forceps 38 from kit 100. As shown in FIG. 10, a first tip of the forceps is inserted through adjustment borehole 32 and placed into engagement with the medial cuneiform 6*a*. The second tip of the forceps is placed between the second and third metatarsals and into engagement with the second metatarsal. The forceps may then be clamped until satisfactory reduction of the Lisfranc complex has been achieved.

Figure 11:
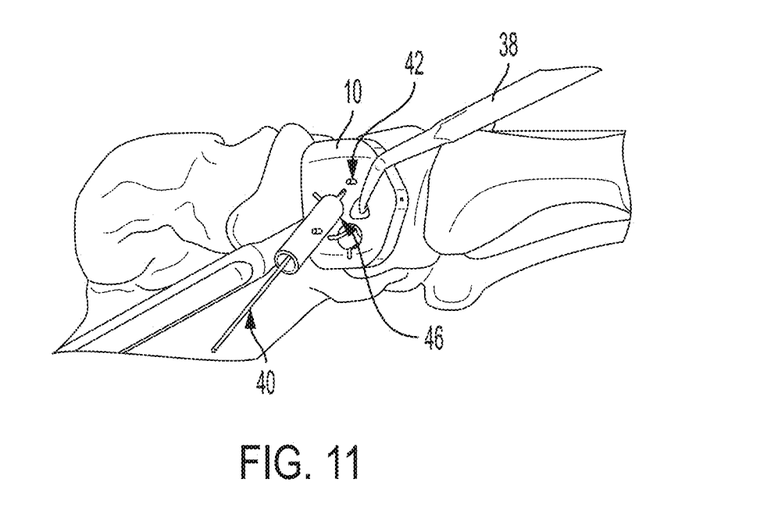

As shown in FIG. 11, a wire guide device 46 is then retrieved from kit 100 and inserted into one of the bone fastening boreholes 30, for example, the superior bone fastening borehole. A guidewire 40 is then inserted through wire guide device 46 and into the skin of the patient. After guidewire 40 has been placed in position, wire guide device 46 is removed and a cannulated drill is placed over the guidewire and used to drill a pilot hole into the medial cuneiform 6*a*, intermediate cuneiform 6*b* and lateral cuneiform 6*c*. Depth gauge 48 may then be retrieved from kit 100 and used to verify that the pilot hole has been drilled to a desired depth. The guidewire 40 may then be removed and a cutting device, such as a scalpel, may be inserted through the cutting slots 36 of superior bone fastening borehole 30 to make small incisions in the patient's skin in order to accommodate seating of the head of bone screw 44. It will be appreciated that the patient's skin may be incised at any time after device 10 has been secured to the foot of the patient and before the bone screw has been inserted into bone, for example, before or after the drilling of the pilot hole. With the desired bone screw in hand, the surgeon may then insert the bone screw entirely through the superior bone fastening borehole 30 and into position to secure the medial cuneiform 6*a*, intermediate cuneiform 6*b* and lateral cuneiform 6*c*. If bone screw 44 is a cannulated screw, the cannulated bone screw may instead be inserted over the guidewire 40 before the guidewire is removed.

Figure 12:
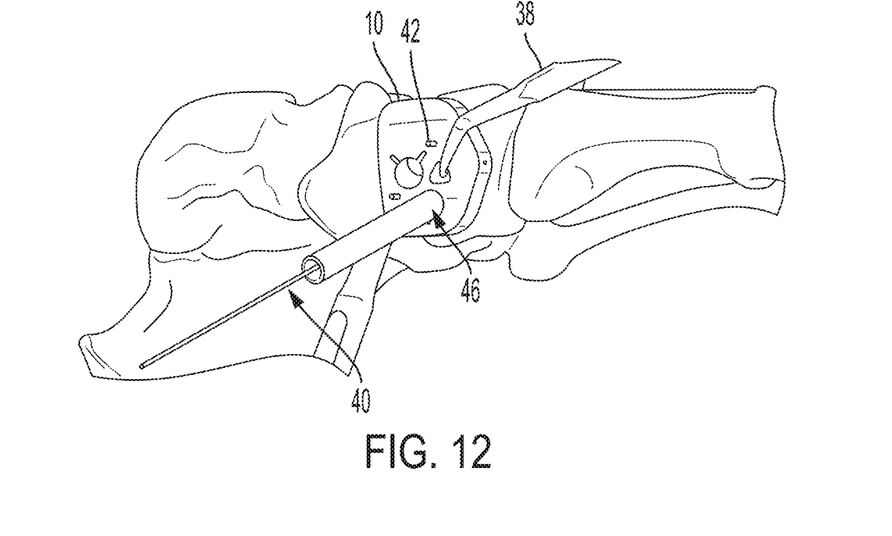

The surgeon may then insert guidewire device 46 into the inferior bone fastening borehole, as shown in FIG. 12, and repeat the process described above. More specifically, guidewire 40 may be inserted through guidewire device 46 to a desired depth. Guidewire device 46 may then be removed and the cannulated drill may be used to drill a pilot hole through the medial cuneiform 6*a* and into the second metatarsal. Depth gauge 48 may again be used to verify that the pilot hole was drilled to a desired depth and to assist the user in choosing a bone screw 44 of proper length. A scalpel, or other cutting device, may be inserted through the cutting slots 36 of inferior bone fastening borehole 30 to make small incisions in the patient's skin, either before or after the pilot hole has been drilled. The surgeon may then insert another bone screw entirely through the device and into bone to secure the medial cuneiform 6*a* and second metatarsal 4*b*.

Figure 13:
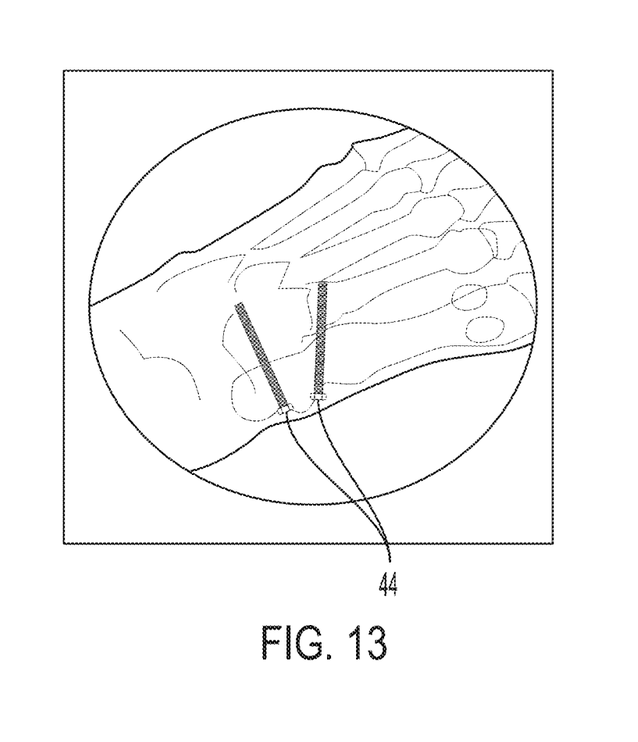
FIG. 13 is a top plan view of a repaired Lisfranc injury depicting internal fixation screws.

FIG. 13 is an x-ray illustrating the positions of bone screws 44 within the patient's treated foot. It will be appreciated that bone screws 44 may be inserted into their respective bones in either order. That is, the bone screw may be inserted and guided through the superior bone fastening borehole either before or after the bone screw is inserted and guided through the inferior bone fastening borehole. After bone screws 44 have been fastened, pins 42 are then removed and device 10 is detached from the patient's foot. One or more bone plates (not shown) may then optionally be secured to the foot of the patient, if necessary, to provide extra support to the treatment area.

The above described embodiment is but one exemplary embodiment specially adapted for guiding an inter-cuneiform bone screw 44 into the medial cuneiform 6a, intermediate cuneiform 6b and lateral cuneiform 6c, and for guiding a Home Run screw through the medial cuneiform 6a and the second metatarsals 4b. Nevertheless, the position and angles of the pin fixation boreholes 28, bone fastening boreholes 30, adjustment borehole 32 and side borehole 34 may be modified depending upon the device's application.

Figure 14:
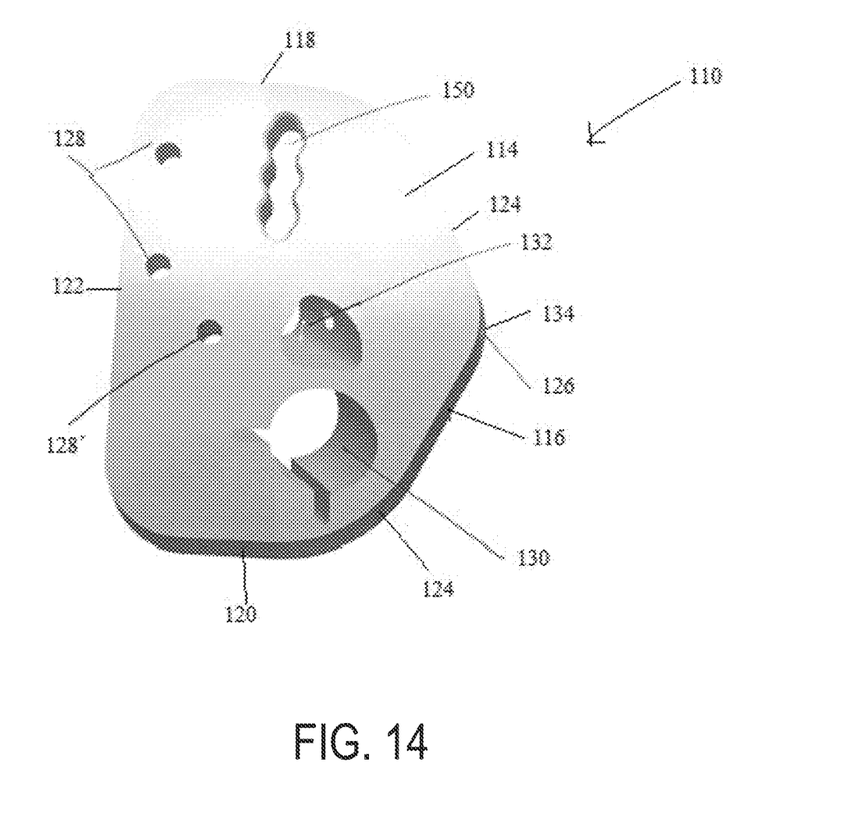
FIG. 14 is a side plan view in a posterior-anterior direction of an alignment and fixation device in accordance with another embodiment of the present invention.

An exemplary modification, as shown in FIG. 14, illustrates an alignment and fixation device 110 in accordance with another embodiment for realigning and fixating displaced bone during a Lapidus procedure. Alignment and fixation device 110 is substantially similar to alignment and fixation device 10, and thus, specific features of device 110 may not described again hereinafter in detail, unless the features are emphasized or unless the features are different than the features previously described with respect to device 10. Instead, when like features are mentioned, the features are renumbered with sequential 100 series numerals. Device 110 has a bone contacting surface 112 (which may be concave), an opposing surface (not shown and which may be convex), a lateral surface 116 disposed between the bone contacting surface and the opposing surface and a longitudinal axis passing through the bone contacting surface and the opposing surface. Device 110 may be pentagonal in shape such that lateral surface 116 defines a superior surface 118, an inferior surface 120, a posterior surface 122, angled surfaces 124 and an anterior corner 126 for assisting a user in positioning device 110 in the proper location on the patient's midfoot.

Like device 10, device 110 defines at least one pin fixation borehole 128, at least one bone fastening borehole 130, an adjustment tool borehole 132 and an alignment index 134 for properly positioning the body of the device on the foot of the patient. Device 110 includes at least two pin fixation boreholes 128. While pin fixation boreholes 128 may be positioned at any location on device 110, an alignment pin fixation borehole 128' is preferably positioned at the midline of the device and adjacent the posterior surface 122 of the body for assisting in the alignment of the device as discussed below.

Bone fastening borehole 130, adjustment tool borehole 132 and alignment index 134 of device 110 are generally similar to bone fastening borehole 30, adjustment tool borehole 32 and alignment index 34 of device 10, and therefore, are not discussed again in detail. It is noted, however, that bone fastening borehole 130 is more akin to the inferior bone fastening borehole of device 10 than the superior bone fastening borehole. It will also be appreciated that while alignment index 134 is again illustrated as a side hole, the alignment index may also be any of the alternative alignment indexes discussed above with respect to alignment and fixation device 10.

Alignment and fixation device 110 further include a rotation slot 150 extending completely through the body of the device from the opposing surface 114 of the device to the bone contacting surface of the device. Rotation slot 150 is preferably positioned approximately halfway between the posterior surface 122 and the anterior corner 126 of device 110 and extends from a location adjacent superior surface 118 toward inferior surface 120 of the device. However, rotation slot 150 need not be positioned approximately halfway between posterior surface 122 and anterior corner 126 of device 110 so long as the rotation slot is at least partially positioned anterior the alignment pin fixation borehole 128'. In one exemplary embodiment, rotation slot 150 is formed by a series of interconnecting holes extending in the superior-inferior direction. Each one of the holes being sized and configured to sequentially receive pin, or similar tool, as described in further detail below.

Use of alignment and fixation device 110 in performing a Lapidus bunionectomy will now be described. Initially, a first guidewire 140 is inserted through side hole 134 until the distal end of the guidewire is positioned within adjustment borehole 132. The surgeon may then place a second guidewire 140 percutaneously into the first tarsometatarsal joint of the patient's foot before sliding device 110 over the second guidewire (such that the second guidewire is slid through alignment pin fixation borehole 128' and the bone contacting surface 112 of device 110 contacts the skin of the patient). Device 110 may then be rotated, as necessary, to align the first guidewire with the bisection of the first metatarsal 4a. Of course, device 110 may be alternatively aligned using any of the aforementioned alignment indexes 134.

After device 110 has been properly positioned and aligned on the foot of the patient, the surgeon may insert fixation pins 142 into pin fixation boreholes 128, through the patient's skin and into bone to temporarily secure the device to the midfoot of the patient. The pins may be bent or trimmed in order to improve access to bone fastening borehole 130, adjustment borehole 132 and rotation slot 150.

A first tip of the forceps may then be inserted through adjustment borehole 132 and placed into engagement with bone while a second tip of the forceps is placed between the second and third metatarsals and into engagement with the second metatarsal. The forceps are then clamped until sufficient reduction has been achieved (e.g., lateral displacement of the first metatarsal 4a toward the second metatarsal).

A pin, or pin-like device, may then be inserted through one of the holes forming rotation slot 150 at a location superior to the first metatarsal 4a. The pin may then be used in a similar manner as a joystick and pulled in an inferior direction for rotating the first metatarsal and correcting the frontal plane alignment of the sesamoid complex. If further adjustment is necessary, the pin may then be moved to another one of the holes that forms rotation slot 150, and that is located inferiorly to the hole in which the previous adjustment was made, before the pin is again pulled in the inferior direction. This process may be repeated as many times as necessary until sufficient frontal plane correction has been achieved. It will be appreciated that the frontal plane correction may be performed before, concurrently or after the reduction step.

After first metatarsal 4a has been properly realigned relative to medial cuneiform 6a, bone screw may be inserted through bone fastening borehole (e.g., with the assistance of guidewire, wire guide, depth gauge, scalpel and a cannulated drill) as described above with respect to device 10. Specifically, bone screw may be inserted through the first metatarsal and through cuneiform bone to fixate the realigned bone in place.

Although the invention herein has been described with reference to particular embodiments, it is to be understood that these embodiments are merely illustrative of the principles and applications of the present invention. It is therefore to be understood that numerous modifications may be made, and are encouraged to be made, to the illustrative embodiments and that other arrangements may be devised without departing from the spirit and scope of the present invention as defined by the appended claims.

The invention claimed is:

1. An alignment and fixation system comprising:
   an alignment and fixation device including a surface adapted to be placed against a foot, a first hole, a second hole, and a third hole;
   a first pin placed through the first hole to secure the alignment and fixation device to a first portion of the foot;
   a second pin placed through the second hole to secure the alignment and fixation device to a second portion of the foot;
   an adjustment device attached to the alignment and fixation device, the adjustment device for adjusting the bone from a misaligned position to an aligned position; and
   a first fastener sized and shaped to be passed completely through the third hole to
   secure the bone in the aligned position, the first fastener including a head and a shaft,
   wherein the third hole is larger than the first and second holes.

2. The system of claim 1, wherein the adjustment device is a forceps including a first tip sized to be disposed at least partially into a tool borehole of the alignment and fixation device.

3. The system of claim 1, wherein the first and second pins are k-wires.

4. The system of claim 1, wherein the first pin includes a first tip for insertion into bone and the second pin includes a second tip for insertion into bone.

5. The system of claim 1, further comprising a third pin placed through a fourth hole of the alignment and fixation device and into a third portion of the foot.

6. The system of claim 1, further comprising a second fastener sized and shaped to be passed completely through a fourth hole of the alignment and fixation device to secure the bone in the aligned position.

7. The system of claim 1, further comprising a wire guide device sized to fit within the third hole.

8. The system of claim 7, further comprising a drill for drilling a pilot hole.

9. The system of claim 1, wherein at least one of the first, second or third holes includes a slot for receiving a cutting instrument.

10. An alignment and fixation system comprising:
    an alignment and fixation device including a surface adapted to be placed against a foot, a first hole, a second hole, a third hole, and a fourth hole;
    a first pin placed through the first hole to secure the alignment and fixation device to a first portion of the foot;
    a second pin placed through the second hole to secure the alignment and fixation device to a second portion of the foot;
    an adjustment device attached to the alignment and fixation device, the adjustment device for adjusting a bone from a misaligned position to an aligned position;
    a first fastener sized and shaped to be passed completely through the third hole to secure the bone in the aligned position, the first fastener including a first head and a first shaft; and
    a second fastener sized and shaped to be passed completely through the fourth hole to secure the bone in the aligned position, the second fastener including a second head and a second shaft,
    wherein the third and fourth holes are larger than the first and second holes.

11. The system of claim 10, wherein the adjustment device is a forceps including a first tip sized to be disposed at least partially into a tool borehole of the alignment and fixation device.

12. The system of claim 10, wherein the first and second pins are k-wires.

13. The system of claim 10, wherein the first pin includes a first tip for insertion into bone and the second pin includes a second tip for insertion into bone.

14. The system of claim 10, further comprising a third pin placed through a fifth hole of the alignment and fixation device and into a third portion of the foot.

15. The system of claim 10, further comprising a wire guide device sized to fit within the third and fourth holes.

16. The system of claim 15, further comprising a drill for drilling a pilot hole.

17. The system of claim 1, wherein one of the first, second, third or fourth holes includes a slot for receiving a cutting instrument.

* * * * *